US005380315A

United States Patent [19]

Isono et al.

[11] Patent Number: 5,380,315

[45] Date of Patent: Jan. 10, 1995

[54] MIXING APPARATUS

[75] Inventors: Keinosuke Isono, Saitama; Tatsuo Suzuki, Tokyo, both of Japan

[73] Assignee: Material Engineering Technology Laboratory Incorporated, Tokyo

[21] Appl. No.: 9,073

[22] Filed: Jan. 26, 1993

[30] Foreign Application Priority Data

Feb. 4, 1992 [JP] Japan .................................. 4-048060

[51] Int. Cl.[6] ........................ A61B 19/00; A61M 5/32

[52] U.S. Cl. ...................................... 604/416; 604/83; 604/86; 604/87; 604/92; 604/82; 604/410; 604/408; 604/403

[58] Field of Search ........................ 604/56, 82, 83, 84, 604/85, 86, 87, 88, 89, 91, 92, 416, 403, 408, 410

[56] References Cited

U.S. PATENT DOCUMENTS

| | | | |
|---|---|---|---|
| 3,785,481 | 1/1974 | Allet-Coche | 604/416 |
| 3,796,303 | 3/1974 | Allet-Coche | 604/416 |
| 3,809,225 | 5/1974 | Allet-Coche | 604/416 |
| 3,917,063 | 11/1975 | Chibret et al. | |
| 4,583,971 | 4/1986 | Bocquet et al. | 604/88 |
| 4,589,879 | 5/1986 | Pearson | 604/88 |
| 4,871,354 | 10/1989 | Conn et al. | 604/416 |
| 5,226,878 | 7/1993 | Young | 604/416 |

FOREIGN PATENT DOCUMENTS

| | | |
|---|---|---|
| 285424 | 10/1988 | European Pat. Off. . |
| 363770 | 4/1990 | European Pat. Off. . |
| 395758 | 11/1990 | European Pat. Off. . |
| 8303540 | 10/1983 | WIPO . |
| 8503432 | 8/1985 | WIPO . |

*Primary Examiner*—Randall L. Green
*Assistant Examiner*—P. Zuttarelli
*Attorney, Agent, or Firm*—Cushman, Darby & Cushman

[57] ABSTRACT

An apparatus is provided for separately storing and selectively mixing a first component, which is in a liquid form, and a second component. The apparatus is formed of a first container made of a flexible material, having a communication mouth with an isolator and adapted to store the first component therein, a supporting case connected to the communication mouth, a second container having a mouth portion held in the case and a plug fitted in the mouth portion and adapted to store the second component, and a hollow, inflexible communication device capable of penetrating through the isolator and the plug. The communication device is accommodated in the first container and is attached to the communication mouth movably therein. The first and second containers can therefore be communicated with each other in a liquid-tight fashion by externally pressing the communication device toward the second container so that the first and second components can be mixed together without changing the positional relationship between the first and second containers.

9 Claims, 10 Drawing Sheets

MIXING APPARATUS

BACKGROUND OF THE INVENTION

1. Field of the Invention

This invention relates to a mixing apparatus suitable, for example, as a container for a medical solution in drip infusion. The mixing apparatus is useful in the field of medical treatment.

2. Description of the Related Art

To administer a powdered drug or lyophilized drug such as an antibiotic or an anticarcinostatic substance to a patient at a medical institution such as a hospital, it has heretofore been the practice to dissolve the drug, which is stored in a container such as a vial, and then to administer the resulting medical solution by drip infusion. In this case, the container with the drug stored therein and a container, in which a dissolving solution for the drug is stored, are connected together by a connecting device such as a double-ended needle or a tubular connector, whereby the dissolving solution is transferred to the former container to dissolve the drug. This handling is however cumbersome and time-consuming and, moreover, the formation of a connecting hole through the drug container may permit the entry of outside air, resulting in the potential danger that the drug inside the drug container could be contaminated.

With a view toward eliminating the above problems, i.e., the cumbersome mixing procedure and the potential danger of contamination, attempts have therefore been made to provide a single-piece apparatus formed in combination of a drug container and a dissolving solution container. Containers for a medical solution have been proposed accordingly, including that disclosed in Japanese Language Laid-Open Publication (PCT) No. 501129/1986 (International Publication No. WO 85/03432) in which a capsule with a vial as a drug container stored therein and a flexible container having a solution outlet and containing a dissolving solution therein are connected together by a tube. Provided inside the tube are a hollow spike needle on a side of the vial and a breakable member on a side of the flexible container. The breakable member blocks a passage in the tube so that the dissolving solution is prevented from flowing through the tube.

Upon administration, the vial inside the capsule is pushed down to have the spike needle penetrate through a rubber plug of the vial, so that the flexible container and the vial are connected together first of all. The breakable member in the tube is then broken by hand so that the passage in the tube is communicated to mix the dissolving solution with the drug.

Although the medical solution container disclosed in Japanese Language Laid-Open Publication (PCT) No. 501129/1986 is improved in the potential danger of contamination from the outside upon communication of the drug container with the flexible container, the latter container being filled with the dissolving solution, to mix the dissolving solution with the drug, the vial itself is caused to slide in the drug container upon the communication so that the surface of the vial has to slide over a large area. Maintenance of high-level tightness is therefore not very easy structurally. Further, the passage must be opened by breaking the breakable member to open the passage after piercing the rubber plug of the vial with the spike needle. Substantial labor is therefore still required. If the breakable member is broken incomplete, the solution has difficulty in flowing through the passage, resulting in the problem that substantial time may be required for the dissolution.

Medical solution containers such as that disclosed in Japanese Patent Laid-Open No. 1277/1990 have also been proposed as further improvements. This medical solution container comprises a flexible container containing a dissolving solution or a diluting solution therein and having a closure-equipped liquid passage portion at an uppermost end thereof, a capsule connected to the flexible container, a drug container held in the capsule and having a mouth portion hermetically sealed with a pierceable plug, and a communication means for communicating the interior of the flexible container with the interior of the drug container. The communication means in turn comprises a hollow spike needle, which has a hub at an intermediate point thereof and bevels at opposite ends thereof, and a brake means for controlling the sequence of communication such that the closure of the flexible container is pierced by one of the bevels of the spike needle after the plug of the drug container has been pieced by the other bevel of the spike needle.

Although the medical solution container disclosed in Japanese Patent Laid-Open No. 1277/1990 offers a reduction in the potential danger of contamination upon communication of the drug container with the flexible container, the latter container being filled with the dissolving solution, to mix the dissolving solution with the drug and also in the laborious handling required upon the communication and mixing, sliding of the drug container itself is required upon the communication as in Japanese Language Laid-Open Publication (PCT) No. 501129/1986 referred to above so that it is structurally difficult to achieve complete tightness. The communication means requires a hollow spike needle, which has a hub at an intermediate point thereof and bevels at opposite ends thereof, and a complex structure for controlling the sequence of communication, e.g., the closure of the flexible container is pierced by one of the bevels of the spike needle after the plug of the drug container has been pierced by the other bevel of the spike needle. The medical solution container therefore requires a greater number of parts, leading to the problems that its production cost is high and the rate of occurrence of handling troubles is high.

SUMMARY OF THE INVENTION

With the foregoing in view, the present invention has as a primary object the provision of a compact mixing apparatus which permits liquid-tight, sure and easy communication of a first container, said first container storing a first component such as a dissolving or diluting solution, with a second container, said second container storing a second component such as a drug, to enable mixing of the first component and the second component in a short time subsequent to the communication and which is substantially simplified in structure.

To attain the above object, the present invention provides an apparatus for separately storing and selectively mixing a first component, which is in a liquid form, and a second component. The apparatus is formed of a first container made of a flexible material, having a communication mouth with an isolator and adapted to store the first component therein, a supporting case connected at an end thereof to the communication mouth of the first container, a second container having a mouth portion held in the supporting case and a plug fitted in the mouth portion and adapted to store the second component, and a hollow, inflexible communication device capable of penetrating through the isolator and the plug to communicate the first container and the second container with each other. The communication device is accommodated in the first container, is attached to the communication mouth movably therein and preferably has a flange portion at an end thereof on a side of the first container, whereby the first container and the second container can be communicated with each other in a liquid-tight fashion by externally pressing the communication device toward the second container so that the first component and the second component can be mixed together without changing the positional relationship between the first container and the second container.

The apparatus according to the present invention is suitable especially as a container for a medical solution. Since the first container and the second container (for example, a drug container such as a vial) are not moved relative to each other, the overall size of the apparatus is small. In addition, the apparatus requires fewer parts so that it can be easily manufactured at low cost. The first container and the second container are connected together in fixed state so that troubles such as leakage, contamination and the like of the dissolving solution can be prevented completely. The use of the hollow communication device also enables smooth transfer of the dissolving solution in the first container, whereby the mixing of the dissolving solution with the drug in the second container can be achieved in a short time.

DETAILED DESCRIPTION OF THE INVENTION AND PREFERRED EMBODIMENTS

According to the present invention, the communication device is arranged in the flexible container (i.e., the first container; the first container will hereinafter be called "the flexible container") so that the flexible container and the drug container (i.e., the second container; the second container will hereinafter be called "the drug container") can be communicated with each other by causing only the communication device to move without causing the drug container to move toward the flexible container, unlike the conventional art. By causing the communication device to move in the flexible container, the communication device first breaks the isolator of the communication mouth and then penetrates through the plug of the drug container. As a result, the flexible container and the drug container are communicated with each other via the communication device, thereby making it possible to allow the dissolving or diluting solution (hereinafter called the "dissolving solution") in the flexible container to move between the flexible container and the drug container by way of the communication device. Owing to the small sliding area and the simplified structure as described above, the apparatus according to the present invention can achieve a high degree of liquid-tightness and, moreover, can be handled easily.

Owing to the use of the hollow communication device, the flexible container and the drug container can be promptly communicated with each other by causing the communication device to penetrate through the isolator of the communication mouth of the flexible container and also through the plug of the drug container. As the communication takes place through the hollow communication device, the movement of the solution is smooth so that the movement of the liquid by a handling error or the like is not impaired. It is therefore possible to achieve in a short time the mixing of the dissolving solution (i.e., the first component; the first component will hereinafter be referred to as the dissolving solution) and the drug (i.e., the second component; the second component will hereinafter be referred to as the drug) and subsequent to the communication.

Figure 1:
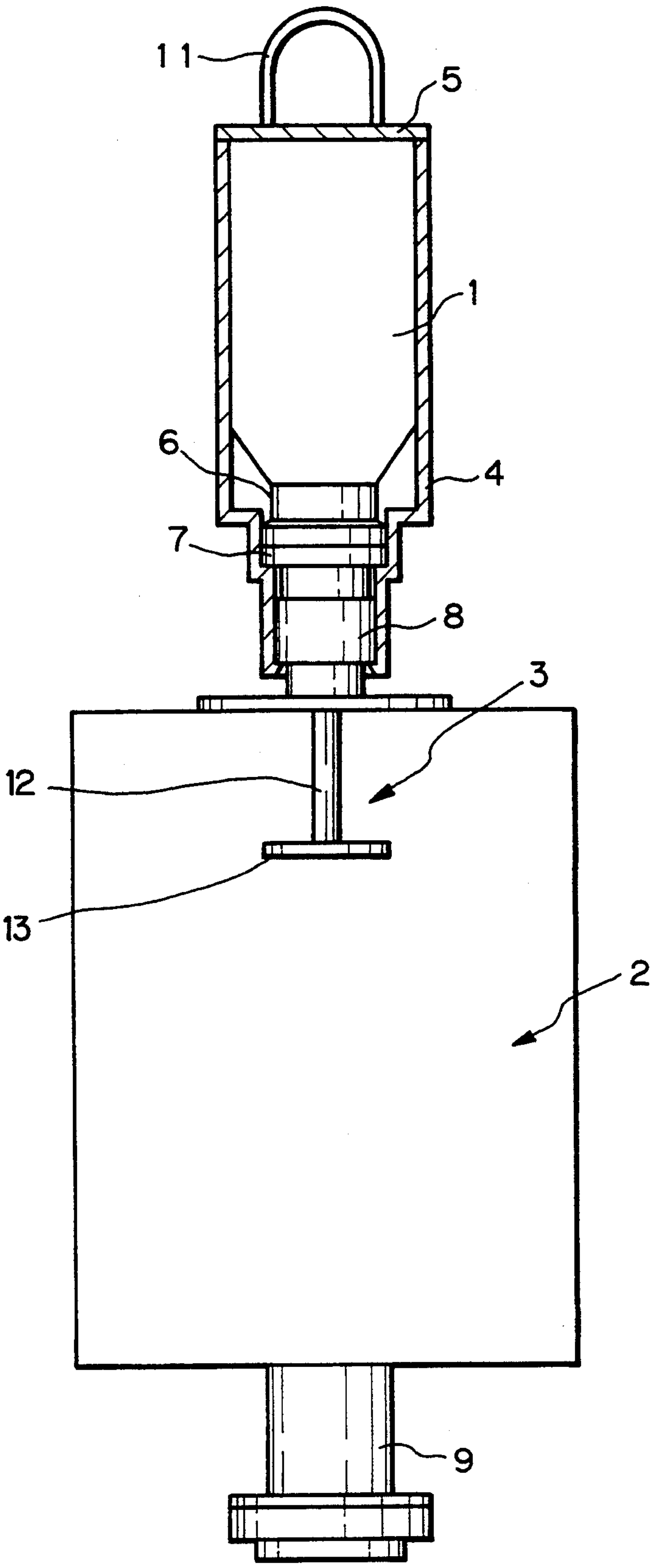
FIG. 1 is a simplified schematic cross-sectional view showing the overall construction of a medical solution container according to a first embodiment of the present invention.
Figure 2:
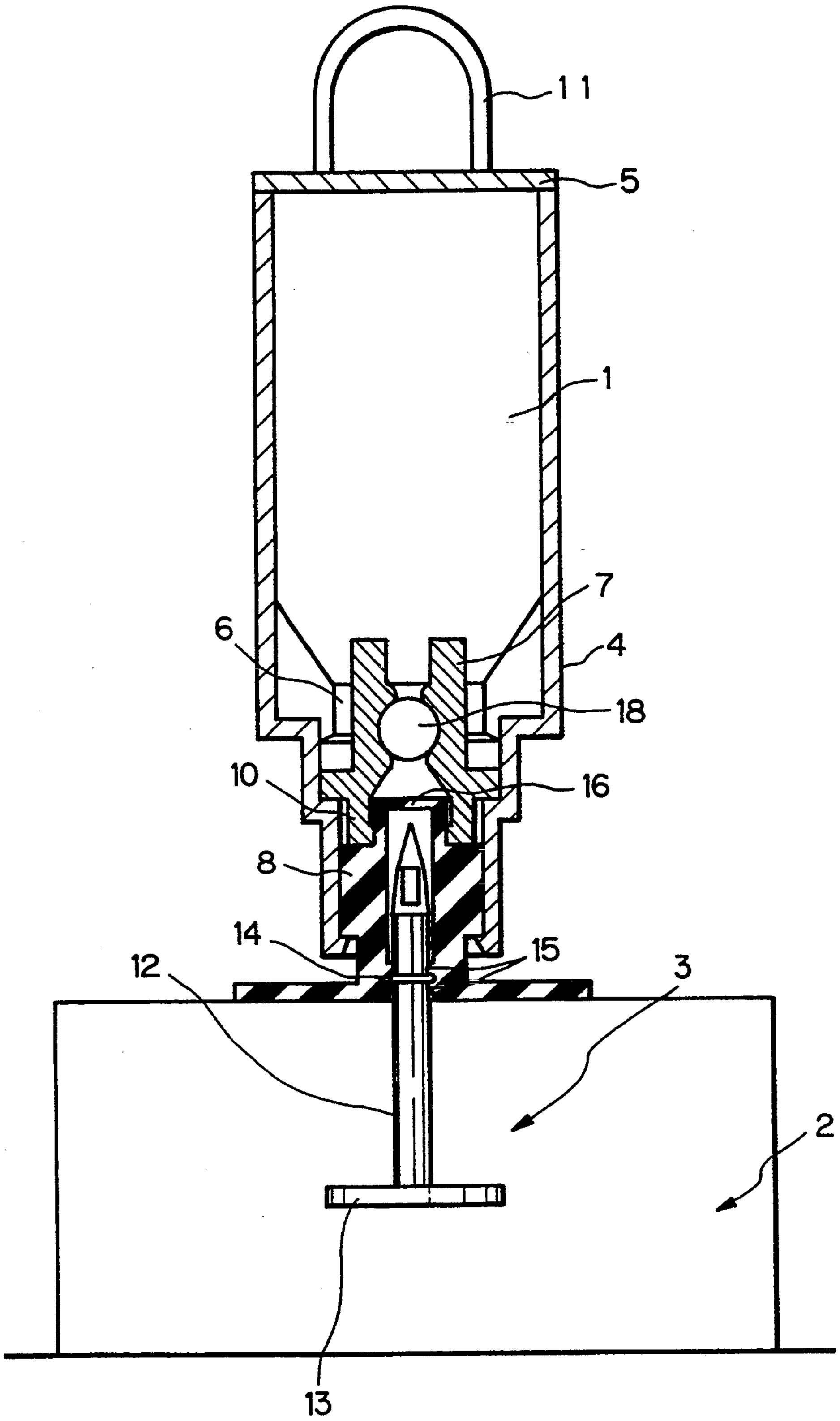
FIG. 2 is a fragmentary schematic cross-sectional view of the medical solution container according to the first embodiment, illustrating the state of a communication mouth before communication.

The medical solution container according to the first embodiment will hereinafter be described with reference to FIGS. 1 through 7. Referring first to FIGS. 1 and 2, the medical solution container is constructed of a drug container 1, a flexible container 2, a communication device 3 and a supporting case 4. The drug container 1 is a container (hereinafter called "the vial") in which a drug such as a powdered or lyophilized drug (or a liquid drug) is stored. The vial 1 is made of glass or plastics, and its mouth portion 6 is sealed by a plug 7. The vial 1 is accommodated in the supporting case 4 with the mouth portion 6 down. Namely, any vial can be used as long as it stores therein a desired substance to be dissolved or diluted and is hermetically sealed by a plug until use. Usable vials include those produced exclusively for particular purposes in addition to known drug vials. Incidentally, the internal capacity of such a vial can generally range from about 20 ml to about 30 ml.

The flexible container 2 is employed to store a dissolving solution. It is formed of a material high in flexibility such as low-density polyethylene, linear low-density polyethylene, polypropylene, a soft polyester, chlorinated polyethylene, polyvinyl chloride or an ethylene-vinyl acetate copolymer. Among these, polyolefins such as low-density polyethylene, linear low-density polyethylene and polypropylene are preferred because they have excellent chemical resistance, are less soluble in the dissolving solution, and are inexpensive and economically excellent. The internal capacity of the flexible container 2 can generally range from about 100 ml to about 200. Its film (wall) thickness can range from about 150 82 m to about 250 μm in general. A laminate film or the like can also be employed depending on the application purpose. The flexible container 2 is provided at an upper end (as labeled in FIGS) thereof with a communication mouth 8 and at a lower end (as labeled in FIGS) thereof with a solution outlet 9. The communication mouth 8 is sealed by an isolator 16. Although a film made of a synthetic resin is used as the isolator 16 in the illustrated embodiment, the isolator 16 may be a plug made of a rubber-like elastic material or the like in various forms. The use of such a film is preferred in handling because it can be easily penetrated by the communication device. Smaller penetration resistance through the isolator of the communication mouth is preferred especially when a plug having relatively large penetration resistance is used as the plug for the vial. The isolator is required only to function as a plug for the dissolving solution in the flexible container. Different from the plug for the powder substance in the vial, no practical problem or inconvenience will arise even when it is not thick.

The supporting case 4 in which the vial 1 is accommodated is open at an upper end (as labeled in FIGS) thereof and is joined to the communication mouth 8 at a lower end (as labeled in FIGS) thereof. The manner of the joining can be fitting, threaded engagement, adhesion or the like. By the supporting case 4, the vial 1 and the communication mouth 8, both stored in the supporting case 4, are fixed and the flexible container 2 is connected to the vial 1. The supporting case 4 is made of a polyolefin resin, a styrene resin, an acrylic resin, a polycarbonate resin, a polyamide resin or the like. Among these, use of polypropylene or methylpentene having relatively high transmission for ultraviolet rays is preferred for easier sterilization because illumination of ultraviolet rays from the outside of the supporting case 4 can sterilize the interior of the supporting case 4.

UV sterilization is effective when it is conducted after the vial and the flexible container have been connected with each other via the supporting case. A germ-free state of the entire medical solution can be ensured. After the connection, it is difficult to apply whole-package sterilization treatment in an autoclave or the like because the content of the vial is in a solid form while the content of the flexible container is in a liquid form. UV sterilization however permits effective sterilization because neither contents are adversely affected.

A cap 5 is applied to the upper end of the supporting case 4. This cap 5 can maintain an aseptic environment within supporting case 4. A suspending means 11 is provided on an upper surface of the cap 5, thereby making it possible to use the medical solution container according to the first embodiment of this invention by hooking it on a hanger or the like.

In the present invention, examples of the drug stored in the vial 1 include cephem antibiotics such as sodium cefazolin and sodium ceftizoxime, penicillin antibiotics such as sodium ampicillin and sodium carbenicillin, antitumor agents such as mitomycin-C and fluorouracil, antiulcer agents such as famotidine and ranitidine hydrochloride, and thrombolytic agents such as urokinase.

Examples of the dissolving solution stored in the flexible container 2 include solutions containing one or more of various electrolytes, in addition to physiological saline, 5% glucose solution, and injection-grade distilled water.

Figure 4:
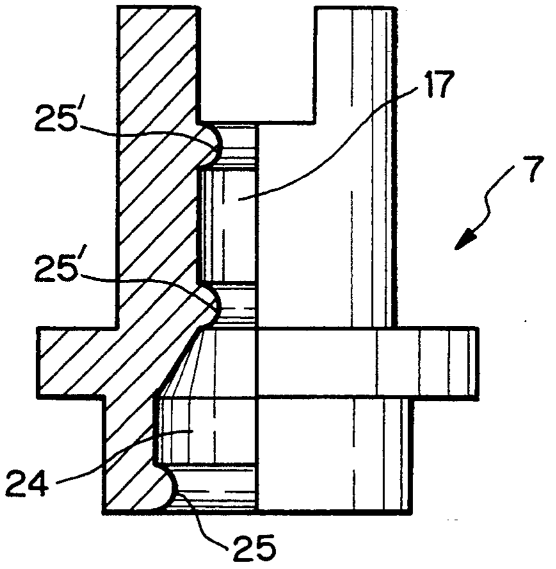
FIG. 4 is a half cross-sectional view of a plug in the medical solution container according to the first embodiment.
Figure 5:
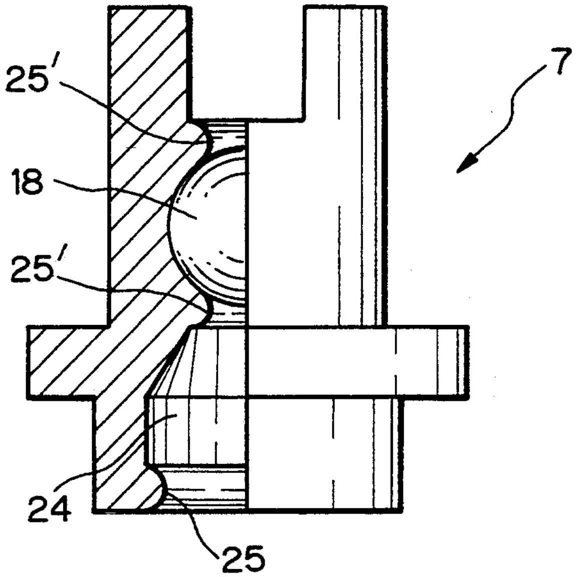
FIG. 5 is a half cross-sectional view of the plug in the medical solution container according to the first embodiment, in which the plug is closed by a stopper.

Details of the plug 7 of the drug container shown in FIG. 2 are illustrated in FIGS. 4 and 5. A passage 17 has been formed in advance through the plug 7 (FIG. 4). This passage 17 is closed by a substantially spherical stopper 18 (FIG. 5). On a side facing the communication device 3 and including a part of the passage 17, the plug 7 is provided with a connecting space 24 in which a recessed cavity is formed. An annular rib 25 is provided in the proximity of an inlet of the connecting space 24. The inner diameter of the annular rib 25 is designed somewhat smaller than the outer diameter of a free end of the communication mouth 8, so that the plug 7 and the communication mouth 8 can be fitted together in a liquid-tight fashion (structure 10 in FIG. 2). This connection structure is suitable for the maintenance of liquid-tightness because, once the vial is connected, it is no longer required to slide or detach the vial.

Annular ribs 25′ serve to hermetically hold the stopper 18 and, after the communication device 3 has penetrated through the passage, also act to prevent leakage of the drug through the passage. Accordingly, the annular ribs 25′ have an inner diameter smaller than the outer diameter of a spike needle 12.

Examples of the material of the plug include the following materials. Preferred illustrative materials for the plug base include, in view of the function as the plug, elastomers such as synthetic rubbers, e.g., isoprene rubber, butadiene rubber, isobutylene-isoprene rubber, styrene-butadiene rubber, chloroprene rubber, silicone rubber, fluorocarbon rubber and ethylenepropylene rubber as well as natural rubber. Corresponding usable illustrative materials for the stopper include synthetic resins such as polypropylene, polyethylene, polystyrene, acrylic resins, polyamides and fluorocarbon polymers, inorganic materials such as glass and ceramics, as well as metallic materials such as aluminum and stainless steel. The above-described elastic materials can also be used as materials for the stopper. In this case, it is desirous to choose the material of the base from the above elastomers other than that employed for the stopper. Certainly, it is preferable to use materials having different moduli of elasticity as the materials for the base and stopper, respectively.

Figure 6:
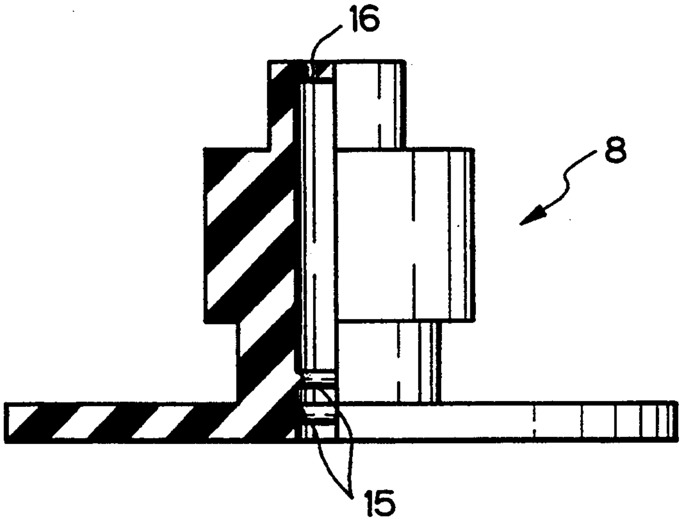
FIG. 6 is a half cross-sectional view of the communication mouth in the medical solution container according to the first embodiment.
Figure 7:
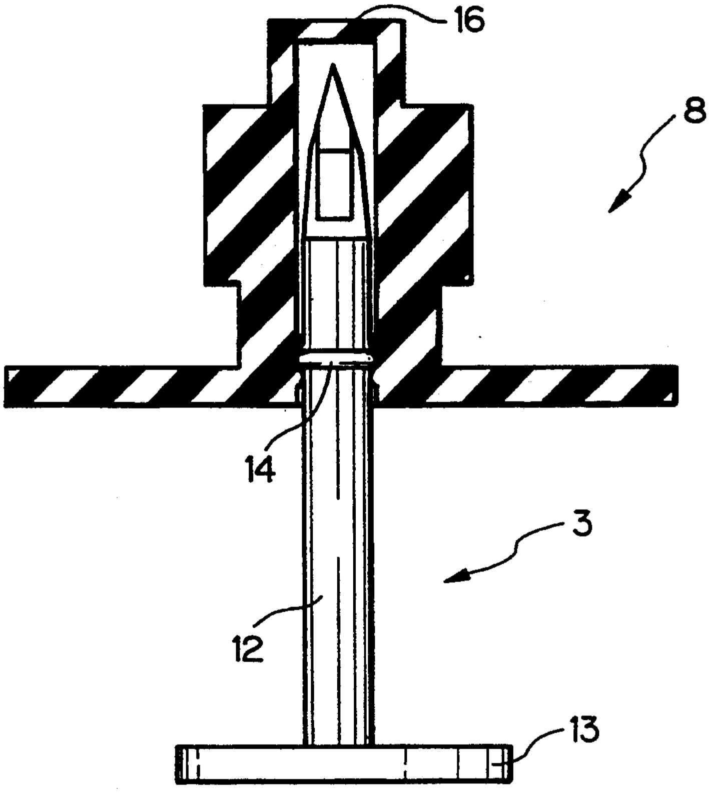
FIG. 7 is a cross-sectional view showing a communication device attached to the communication mouth in the medical solution container according to the first embodiment.

Details of the communication mouth employed in the medical solution container according to the first embodiment are shown in FIG. 6, and details of the communication mouth with the communication device attached thereto are illustrated in FIG. 7. The communication device 3 is composed of the hollow spike needle 12, as a hollow tube, and a flange 13. The communication device 3 is also provided with a rib 14. By the rib 14 and two ribs 15 formed on the communication mouth 8, the communication device 3 is tentatively held in the communication mouth 8. The communication device 3, therefore, does not drop from the communication mouth 8 until the medical solution container is used. Upon use, the flange 13 is strongly pushed to have the rib 14 override the upper rib 15 as viewed in FIG. 7, whereby the communication device 3 becomes movable in the communication mouth 8.

If the inner diameter of the ribs 15 is designed somewhat smaller than the outer diameter of the spike needle 12, the prevention of leakage of the drug through the communication mouth can be made more complete. Liquid-tight fitting of the free end portion of the plug in the free end portion of the communication mouth is sufficient by itself for the prevention of leakage of the drug. More complete prevention of leakage of the drug can, however, be achieved if the portions of the communication mouth and plug, said portions being maintained in contact with the communication device, are also designed as a liquid-tight structure which forms a seal between the communication device and the portions of the communication mouth and plug upon penetration of the communication device 12 through the isolator 16.

Illustrative examples of the material of the communication mouth include polyethylene and polypropylene. Since it is the general practice to join the communication mouth and the flexible container body by heat sealing, impulse sealing, high-frequency welding, ultrasonic welding, an adhesive or the like, it is only necessary to suitably choose a material suitable for the joining method. Usable examples of the material of the communication device 3 include polyethylene, polypropylene, polyamides and ABS resin as well as resin compositions of these resins and an organic filler such as a glass filler.

When plastic materials are used for both the communication mouth and the communication device, it is general to produce them by injection molding. Although the spike needle and flange can be formed integrally as a single-piece element by injection molding, it is also possible to form them as discrete elements and then to fixedly adhere them together with an adhesive. Incidentally, the inner diameter of the spike needle generally ranges from 1.5 mm to 2.5 mm or so and its outer diameter generally ranges from 3 mm to 6 mm or so. Smooth mixing of the dissolving solution with the drug is not feasible if the inner diameter is too small. An unduly large outer diameter, however, leads to greater resistance upon penetration through the isolator of the communication mouth and the plug. The outer diameter of the flange may range from about 8 mm to about 20 mm for easier push and convenient handling. Needless to say, the strength of the flange should be adjusted in view of expected pushing force.

The communication device can be accommodated in the flexible container in such a state that the communication device is tentatively held in the communication mouth as follows: The passage in the communication mouth is sealed at the upper end by the isolator. The communication device is inserted into the open lower end and there held tentatively, thus forming a single unit which is then fused to the connection port located in opposition to the solution outlet of the flexible container in a liquid-tight fashion with an ultrasonic welding device, the protruding end of the communication device having been passed through the connection port without touching it.

Assembly of the above-described medical solution container can be conducted, for example, as will be described next. First, the flexible container having the communication mouth is filled with the dissolving solution and then sealed hermetically. A sterilizing cap is next applied to the communication mouth, followed by sterilization in an autoclave. The drug-filled vial is placed in the supporting case and the cap is then applied to the supporting case. A sterilizing cap is applied to an opening of the supporting case, which opening is located on a side where the supporting case is connected to the communication mouth. The supporting case is then sterilized with ethylene oxide gas. While maintaining the sterilized state, the sterilizing caps are removed from the above-sterilized, vial-filled, supporting case and the sterilized flexible container, respectively, and the sterilized, vial-filled, supporting case and the sterilized flexible container are connected together. Although the inside of the connected portions is maintained in a substantially germ-free state, UV sterilization treatment (250–350 nm, 40 W, 20 minutes or so) can be applied to ensure the germ-free state where the supporting case and the communication mouth have permeability to ultraviolet rays. In this manner, the intended medical solution container can be completed.

Figure 3:
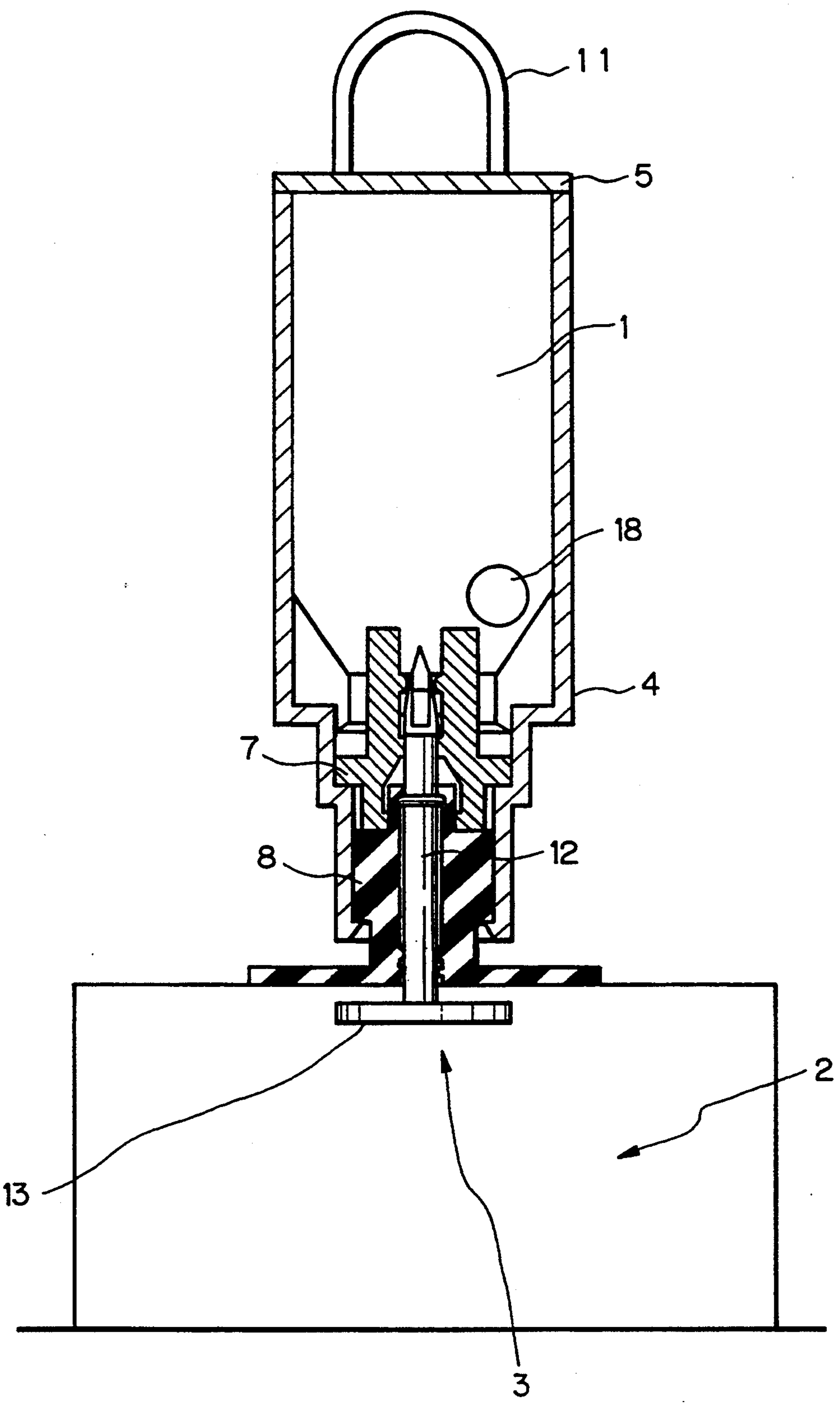
FIG. 3 is a fragmentary schematic cross-sectional view of the medical solution container according to the first embodiment, depicting the state of the communication mouth after communication.

Based on FIG. 3, a description will next be made of how the medical solution container according to the first embodiment of this invention is communicated by the communication device. From the outside of the flexible container 2, the flange 13 is first pushed toward the communication mouth 8. This pushing of the flange 13 can be easily conducted externally by finger pressure through the wall (film) of the flexible container. As a result, the free end of the spike needle 12 is caused to extend through the isolator 16 of the communication mouth. When the flange 13 is pushed further toward the communication mouth 8, the free end of the spike needle 12 pushes the stopper 18 out of the passage 17 into the vial 1 so that the interior of the vial 1 and that of the flexible container 2 are communicated with each other via the communication device 3.

After the vial 1 and the flexible container 2 have been communicated with each other as described above, the flexible container 2 is pressed or squeezed to feed a portion of the internal dissolving solution into the vial 1 whereby the drug inside the vial 1 is dissolved. When the flexible container 2 is pressed or squeezed again, the medical solution inside the vial 1 flows back into the flexible container 2. A solution administration set is then connected to the solution outlet 9 of the flexible container 2 so that the medical solution so returned is administered by transfusion. Use of the suspending means 11 at this time makes it possible to suspend the flexible container 2 from a hanger and to administer the medical solution to a patient through the solution administration set.

Figure 8:
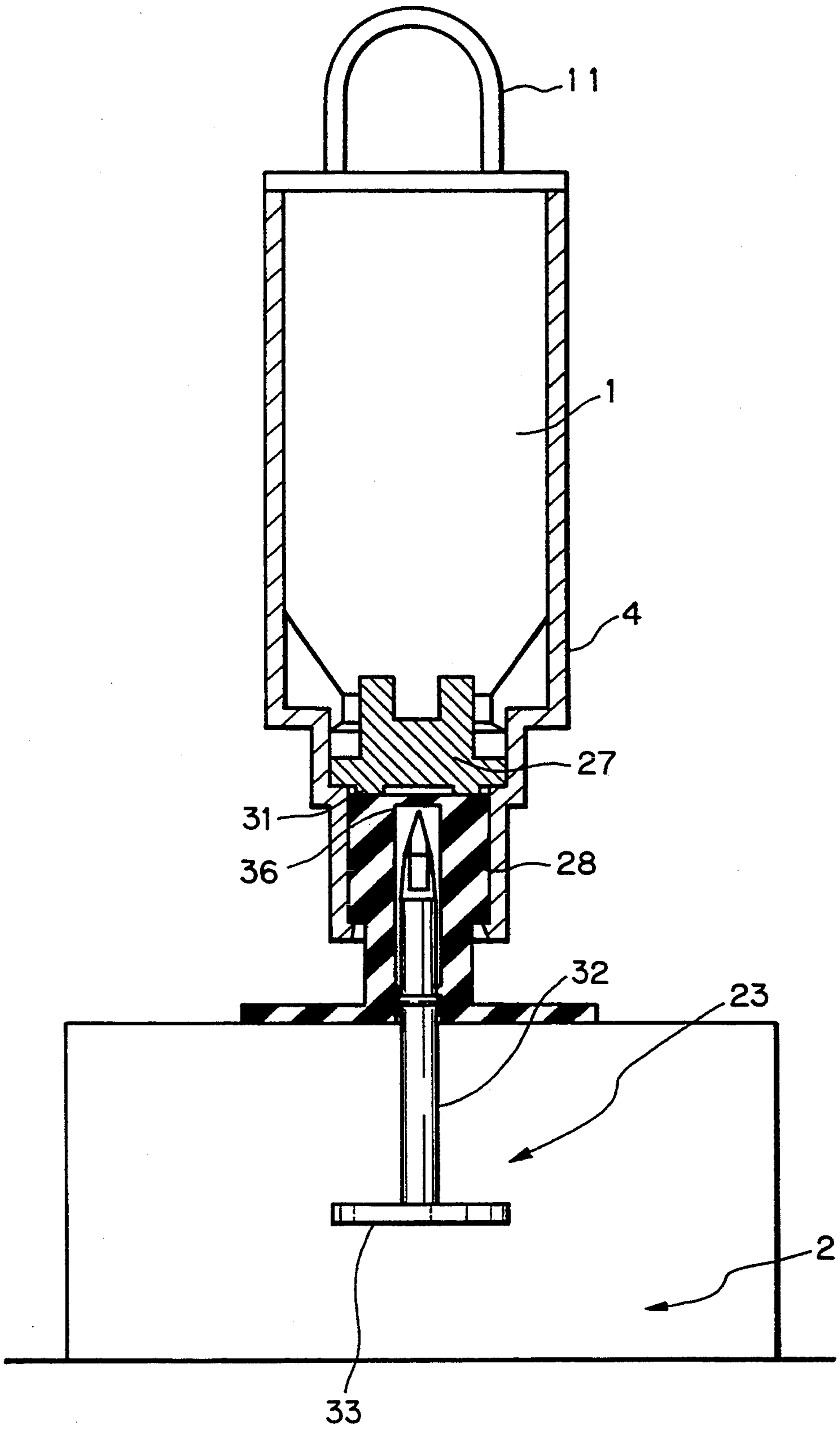
FIG. 8 is a simplified schematic cross-sectional view of a medical solution container according to a second embodiment of the present invention before communication.
Figure 9:
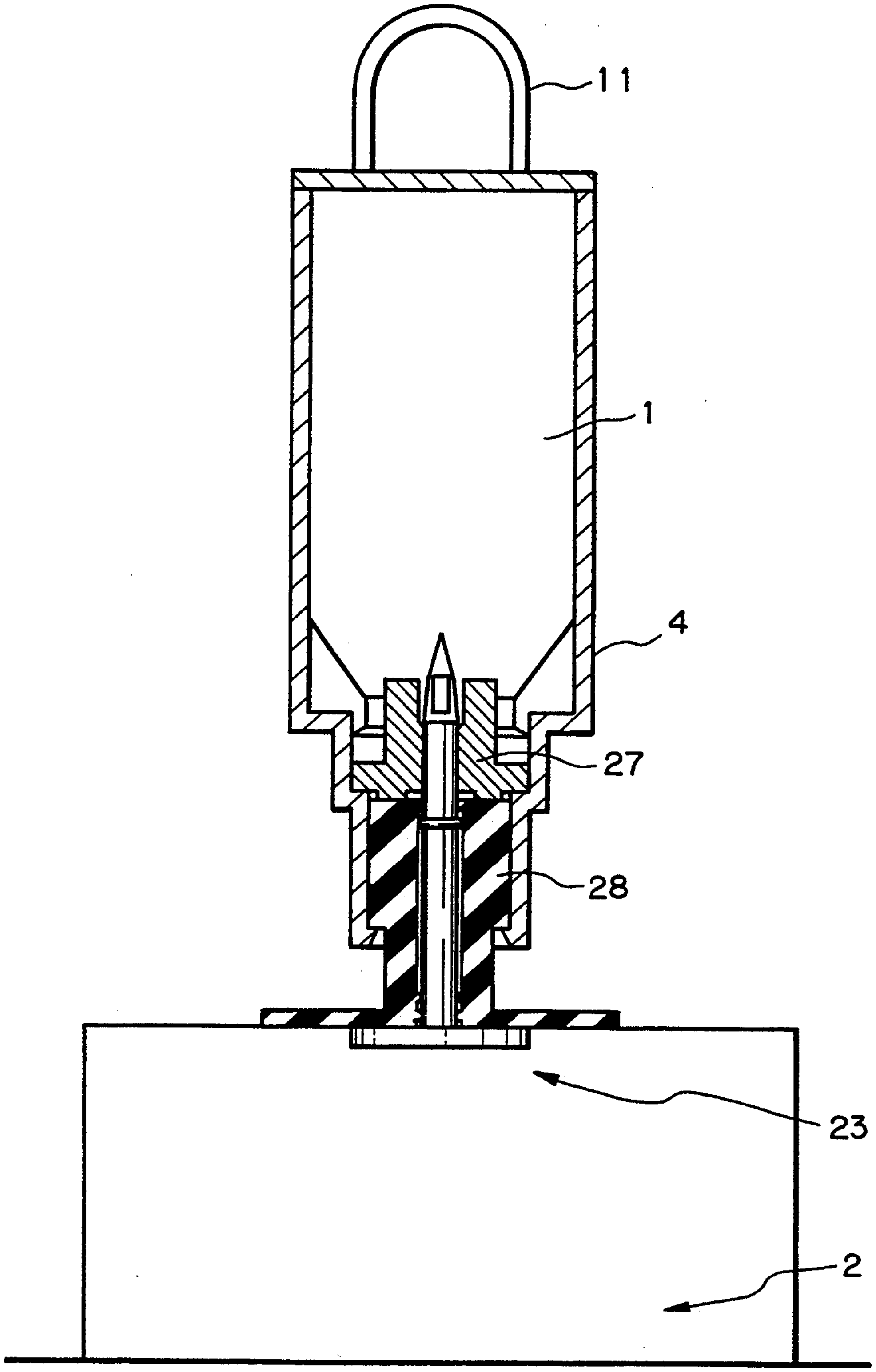
FIG. 9 is a simplified schematic cross-sectional view of the medical solution container according to the second embodiment after communication.
Figure 10:
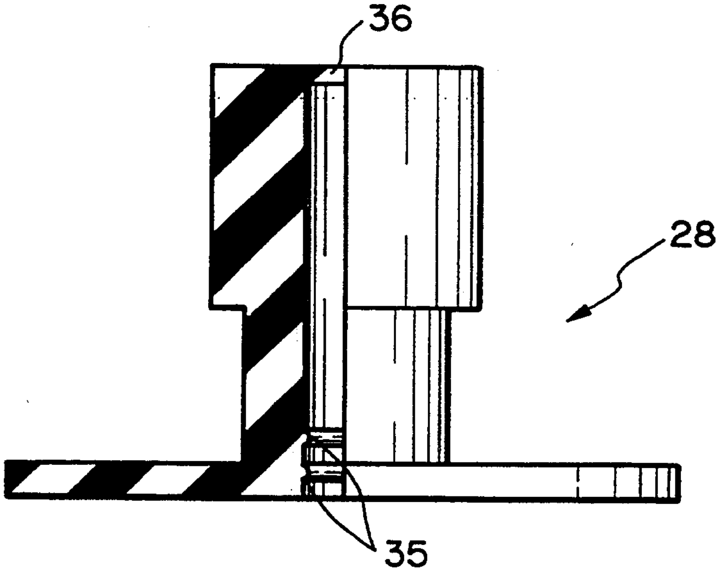
FIG. 10 is a half cross-sectional view of a communication mouth in the medical solution container according to the second embodiment.

The second embodiment of the present invention will next be described with reference to FIGS. 8 and 9. A plug 27 is provided with an annular ridge 31 on a side of a communication mouth 28. The plug 27 and the communication mouth 28 are connected in a liquid-tight fashion owing to the provision of the annular ridge 31. The remaining parts, i.e., the drug container 1, the flexible container 2 and the supporting case 4 are substantially the same as the corresponding elements in the first embodiment. It is, however, necessary to have the communication device 23 very sharply pointed at a free end of the hollow spike needle 32 because the communication device 23 must penetrate through both an isolator 36 of the communication mouth and the plug 27 which is not equipped with a removable spherical stopper. The manner of communication of the medical solution container by the communication device is substantially the same as in the preceding embodiment. First, a flange 33 is pushed toward the communication mouth 28 from the outside of the flexible container 2. The free end of the communication device 23 then pierces the isolator 36 of the communication mouth. Further pushing of the flange toward the communication mouth 28 causes the free end of the communication device 23 to penetrate through the plug 27 so that the inside of the vial 1 and that of the flexible container 2 are communicated with each other via the communication device 23. FIG. 10 illustrates the communication mouth 28 in half cross-section. Differing from the communication mouth shown in FIG. 6, a connecting end to a plug is flat because the plug is provided with the annular ridge 31 and liquid-tightness can be maintained by this structure. This communication mouth has the annulus ribs 35 to tentativelly hold the hollow spike needle.

Figure 11:
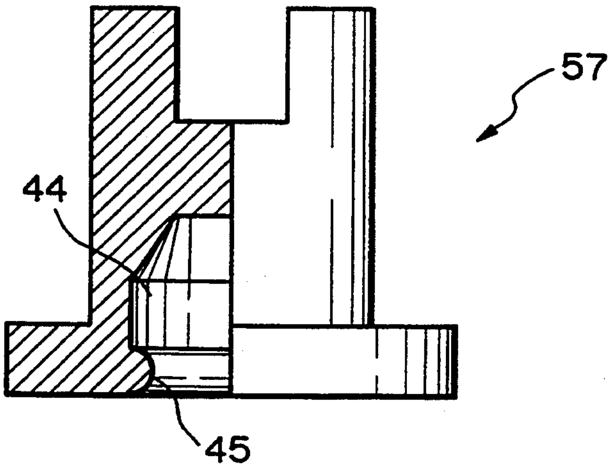
FIG. 11 is a half cross-sectional view of a modification of the plug in the medical solution container according to the first or second embodiment.
Figure 12:
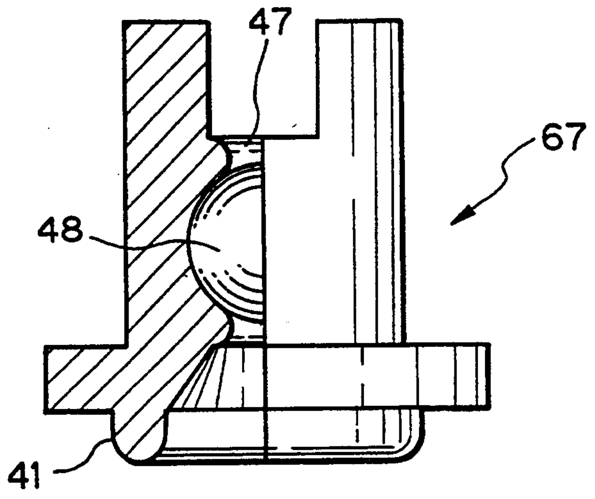
FIG. 12 is a half cross-sectional view of a modification of the plug in the medical solution container according to the first or second embodiment.

Other modifications of the plug, said modifications being usable in the medical solution containers according to the present invention, are illustrated in FIG. 11 and FIG. 12, respectively. A plug 57 shown in FIG. 11 is a rubber plug having a connecting space 44 and an annular rib 45 in order to connect the plug 57 with a communication mouth in a liquid-tight fashion. Further, a plug 67 depicted in FIG. 12 has a passage 47 and a stopper 48 similar to those employed in the plug shown in FIG. 5. The plug 67 has the annular ridge 41. Regarding the structure of the plug usable in the medical solution container according to this invention, plugs other than those shown in FIGS. 11 and 12 can also be used as long as they can satisfy the function as a plug for the vial 1. For example, rubber plugs for vials, said rubber plugs having been employed conventionally, can also be used.

Figure 13:
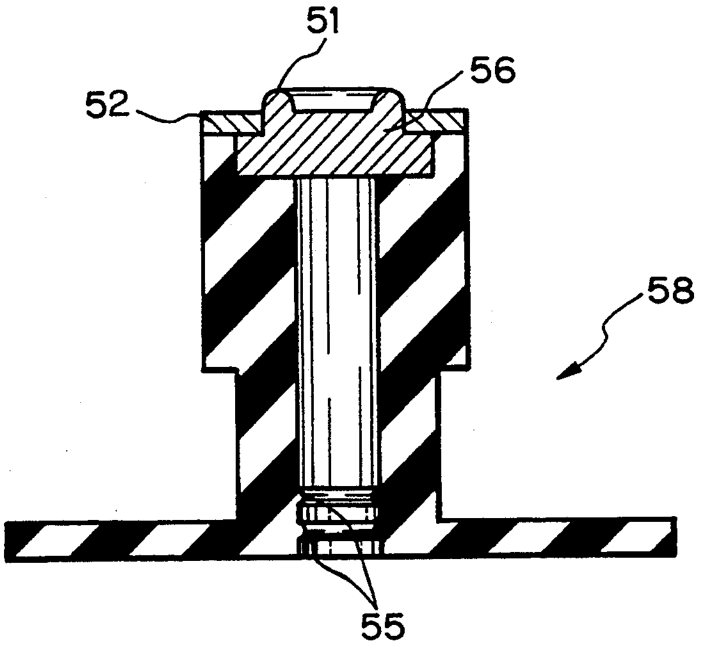
FIG. 13 is a half cross-sectional view of a modification of the communication mouth in the medical solution container according to the first or second embodiment.

Further, a modification of the communication mouth, said modification being usable in each of the medical solution containers of this invention, is illustrated in FIG. 13. As an isolator 56 in a communication mouth 58, a plug made of a rubbery elastomer is used. This isolator 56, which is fixed on the top of the communication mouth 58 with a fixing member 52, is provided with an annular ridge 51 so that the communication mouth can be connected to a plug of the vial 1 in a liquid-tight fashion. The use of the communication mouth 58 in the medical solution container according to this invention can prevent the dissolving solution from leaking into the supporting case 4 even when a drug-filled vial, which has been employed widely, is used, due to the annular ridge 51 fitted in a conventional plug of a vial. This communication mouth also has annular ribs 55.

Figure 14:
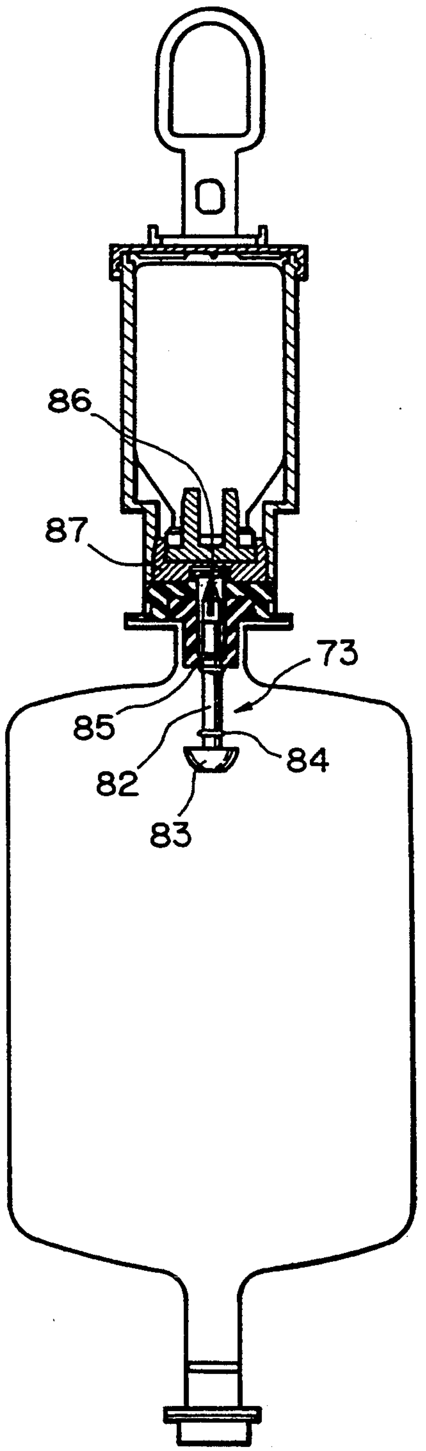
FIG. 14 is a detailed schematic cross-sectional view of a medical solution container according to a third embodiment of the present invention before communication.
Figure 15:
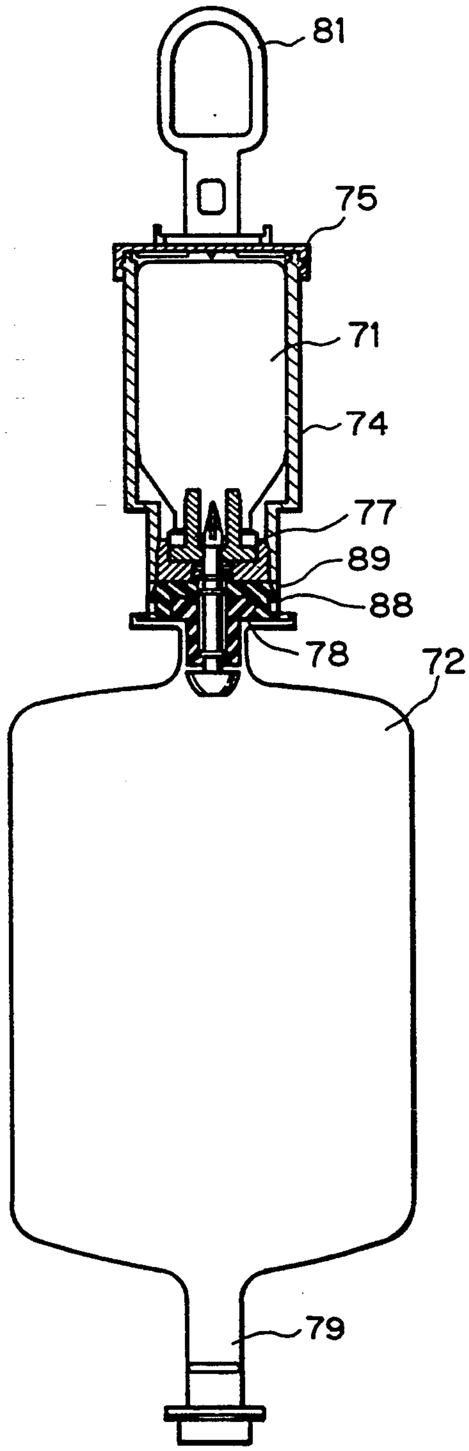
FIG. 15 is a detailed schematic cross-sectional view of the medical solution container according to the third embodiment after communication.

The medical solution container according to the third embodiment of this invention will next be described with reference to FIGS. 14 and 15. In the third embodiment, a fixing member 87 is held between a plug 77 of a vial 71 and a communication mouth 78 of a flexible container 72 as a means for securing a liquid-tight state between the plug 77 and the communication mouth 78. The use of the fixing member 87 makes it possible to surely and easily fix the vial 71 in a supporting case 74. This fixing member 87 functions as a packing which connects the plug 77 and the communication mouth 78 in a liquid-tight state. Namely, detents 88 formed on the communication mouth 78 are designed to fit in corresponding bores 89 formed in the supporting case 74 at positions near a free end of the supporting case 74. The vial 71 is accommodated in the supporting case 74 in which the fixing member 87 has been fitted in advance, and a cap 75 having a suspending means 81 is applied. The flexible container 72 provided with the communication mouth 78 and a solution output 79 is then connected to the supporting case 74, whereby the fixing member 87 is compressed between the plug 77 and the communication mouth 78 so that a liquid-tight state can be readily achieved.

The communication mouth 78 is provided with an annular rib 85, so that a communication device 73 can be tentatively held by the annular rib 85 and three annular ribs 84 provided on a spike needle 82 of the communication device 73. A flange portion 83 of the communication device 73 is formed in such a shape that facilitates being pushed by fingers. For the sake of manufacturing convenience, the communication mouth 78 is formed by the combination of two members. Structurally, it is not absolutely necessary to form it by two members. Communication can be achieved in a similar manner as in the medical solution containers described above. By causing the spike needle 82 of the communication device 73 to penetrate through an isolator 86 of the communication mouth 78, the fixing member 87 and the plug 77, the vial 71 and the flexible container 72 can be easily communicated with each other while maintaining the liquid-tight state. The fixing member 87 can be formed of a material similar to that of the plug 77.

Various embodiments and modifications have been described above. It is however to be noted that the present invention can adopt various changes and modifications without departing from the spirit or scope of the invention.

What is claimed is:

1. An apparatus for separately storing and selectively mixing a first component, which is in a liquid form, and a second component, comprising:

(a) a first container made of a flexible material, having a communication mouth with an isolator and adapted to store the first component therein, said communication mouth having detents formed thereon, (b) a second container having a mouth portion in which a plug is fitted, and adapted to store the second component, (c) a fixing member held between the plug and the communication mouth, (d) a supporting case in which the second container is accommodated, said supporting case having bores formed at a position near a free end thereof, such that the detents fit in the corresponding bores to connect the supporting case to the communication mouth of the first container, whereby the fixing member is compressed to secure a liquid-tight state between the plug and the fixing member and between the mouth and the fixing member, (e) a hollow, inflexible communication device capable of penetrating through the isolator, the fixing member and the plug to communicate the first container and the second container with each other, said communication device being tentatively held in the communication mouth by an annular rib formed thereon, and movable therein, whereby the first container and the second container communicate with each other in a liquid-tight fashion by externally pressing the communication device toward the second container so that the first component and the second component can be mixed together without changing the positional relationship between the first container and the second container.

2. An apparatus of claim 1, wherein the communication device has a flange portion at an end thereof on a side of the first container.

3. An apparatus of claim 1, wherein the communication mouth of the first container and the mouth portion of the second container are connected together in a liquid-tight fashion.

4. An apparatus of claim 1, wherein the first container has a content outlet in addition to the communication mouth.

5. An apparatus of claim 1, wherein the supporting case is additionally provided with a suspending means on an end opposite to that at which the supporting case is connected to the communication mouth of the first container.

6. An apparatus of claim 1, wherein the supporting case is made of a material which permits transmission of ultraviolet rays therethrough.

7. An apparatus of claim 1, wherein the plug has a separable spherical stopper.

8. An apparatus of claim 1, wherein the first component is a dissolving or diluting solution and the second component is a drug; and the apparatus is useful as a container for a medical solution.

9. An apparatus of claim 8, wherein the second container is a vial containing the drug therein.

* * * * *